United States Patent [19]

Kuzmak

[11] Patent Number: 5,449,368
[45] Date of Patent: Sep. 12, 1995

[54] LAPAROSCOPIC ADJUSTABLE GASTRIC BANDING DEVICE AND METHOD FOR IMPLANTATION AND REMOVAL THEREOF

[76] Inventor: Lubomyr I. Kuzmak, 304 E. Northfield Rd., Livingston, N.J. 07309

[21] Appl. No.: 59,592

[22] Filed: May 12, 1993

Related U.S. Application Data

[63] Continuation-in-part of Ser. No. 19,302, Feb. 18, 1993.
[51] Int. Cl.⁶ .............................................. A61B 17/00
[52] U.S. Cl. ................................... 606/157; 606/228
[58] Field of Search ................ 606/151, 157, 201–203; 600/29, 30, 31; 128/899, DIG. 25

[56] References Cited

U.S. PATENT DOCUMENTS

| | | | |
|---|---|---|---|
| 4,592,339 | 6/1986 | Kuzmak et al. | |
| 4,632,114 | 12/1986 | Todd et al. | 128/DIG. 25 |
| 4,696,288 | 9/1987 | Kuzmak et al. | |
| 4,863,985 | 2/1989 | Hill | 606/157 |
| 5,006,106 | 4/1991 | Angelchik | 128/899 |
| 5,074,868 | 12/1991 | Kuzmak | 606/157 |
| 5,152,770 | 10/1992 | Bengmark et al. | 606/157 |
| 5,160,338 | 11/1992 | Vincent | 606/157 |
| 5,226,429 | 7/1993 | Kuzmak | 606/157 |

OTHER PUBLICATIONS

Kuzmak, "Stoma Adjustable Silicone Gastric Banding," Problems in General Surgery, Apr./Jun. 1992, vol. 9, No. 2, pp. 298–317.

*Primary Examiner*—Stephen C. Pellegrino
*Assistant Examiner*—Nancy Mulcare
*Attorney, Agent, or Firm*—Larson and Taylor

[57] ABSTRACT

An adjustable gastric banding device for regulating the size of a stoma opening in the stomach of a patient includes an elongate band portion that encircles the stomach so as to limit the food intake by the digestive portion of the stomach. The device can be readily implanted and removed using laparoscopic procedures. A locking element protruding from a location near the distal end of the encircling band portion is inserted into a slot formed in a receiving segment at an intermediate location along the encircling band portion so as to form a circle or loop of fixed diameter. The receiving segment has a thickness which is greater than the thickness of the encircling band portion and of the rear portion of the band. A moveable bolt secures the locking element in the slot. The bolt can be displaced remotely, thus releasing the locking element and allowing easy laparoscopic removal of the banding device. The entire circumference of the stomach encircling band portion is covered by an expandable section in contact with the surface of the stomach. The size of the stoma opening can be adjusted by injecting into or removing fluid from the expandable section.

40 Claims, 4 Drawing Sheets

LAPAROSCOPIC ADJUSTABLE GASTRIC BANDING DEVICE AND METHOD FOR IMPLANTATION AND REMOVAL THEREOF

CROSS REFERENCE TO RELATED APPLICATIONS

This application is a continuation-in-part of my application Ser. No. 08/019,302, filed on Feb. 18, 1993, entitled "Adjustable Gastric Banding Device."

FIELD OF THE INVENTION

The present invention relates to a device for the treatment of morbid obesity, and, in particular, relates to gastric banding devices which encircle a portion of the stomach to form a stoma opening of reduced diameter so as to restrict food intake.

DESCRIPTION OF THE PRIOR ART

In the previously known stoma adjustable silicone gastric banding (SASGB), disclosed in U.S. Pat. No. 4,592,339 (Kuzmak et al.), which is hereby incorporated by reference, an inflatable or expandable section of a gastric band covers a portion of the circle defined by the band. The expandable section of the device permits some adjustment of the size of the stoma opening both intraoperatively and postoperatively. This device is simple in construction and enables the desired diameter of the stoma opening to be maintained. U.S. Pat. No. 4,696,288 (Kuzmak et al.), which is also hereby incorporated by reference, discloses a calibrating apparatus which facilitates controlling the size of the stoma with a gastric band.

Even with the ability to adjust the stoma size, it may still be desirable in given situations, e.g., obstruction of the stoma from edema and migration of the band to remove the band entirely when deflation is insufficient to relieve the condition. A scheme for enabling gastric bands to be removed is discussed in U.S. Pat. No. 5,074,868 (Kuzmak), which is hereby incorporated by reference. When a remotely situated pull cord is retracted, a suture cutting blade severs sutures securing overlapping portions of the band which encircle the stomach. Another removable gastric band device is disclosed in U.S. Pat. No. 5,160,338 (Vincent).

A laparoscopic gastric band and a method for using such a band is disclosed in U.S. Ser. No. 07/719,123, filed Jun. 20, 1991, in the name of Lubomyr I. Kuzmak. Reference is also made to Lubomyr I. Kuzmak, "Stoma Adjustable Silicone Gastric Banding," Problems in General Surgery, Volume 9, No. 2, J. B. Lippincott Co., April/June 1992.

Although the devices disclosed in the Kuzmak and Kuzmak et al patents and patent application referred to above have proven to be successful in practice, some potential disadvantages remain. For example, the belt-like band construction of the devices wherein one end of the band fits through a buckle at the other end can be difficult to tighten, and bulges are created at the ends of the inflated or expanded section (caused by the fact that the expanded section only partially extends around the circumference of the band), thereby resulting in localized compression of the stomach wall. Further, the parts of the band must be sutured together when the band is placed at a desired position around the stomach and this suturing can be difficult to carry out.

SUMMARY OF THE INVENTION

It is an object of the present invention to provide a laparoscopic SASGB which is more effective in providing uniform modification of the stoma size, is less invasive to the stomach wall, and is also easily reversible.

It is a further object of the present invention to provide a laparoscopic gastric band positioned around the stomach which includes a locking element secured by a remotely removable device which eliminates or substantially reduces the discomfort caused to some patients by related devices.

It is another object of the present invention to eliminate bulging associated with SASGB devices of the prior art and thus eliminate localized compression of the stomach wall.

It is a further object of the present invention to eliminate the need for suturing of the band together in order to secure the band at a desired position around the stomach.

It is a further object of the present invention to provide a SASGB having an increased range of stoma adjustment.

In accordance with a one aspect of the invention, a gastric banding device is provided for forming a stoma opening in a stomach so as to restrict food intake to the lower digestive portion of the stomach and which is particularly adapted for use in, but not limited to, laparoscopic implantation and removal of the device. According to a preferred embodiment thereof, the device comprises: an elongate band member including a band portion for, in use, encircling a stomach to form a stoma opening in the stomach, the band member including a free end; an expandable section secured to the band portion of the band member for varying the size of the stoma opening; a securing member located near the free end of the band member and protruding outwardly therefrom; a recess, formed in an intermediate portion of the band member segment having a thickness greater than the thickness of the remainder of the band member, for receiving the securing member therein; and means for retaining the securing member in the recess so that the band portion forms a circle of a predetermined fixed diameter around the stoma opening.

Advantageously, the retaining means comprises a moveable threaded bolt, and in a preferred embodiment, the securing member includes a threaded hole therein in which the bolt is received. The bolt preferably comprises a distal part of an elongate control element located within the band member and extending longitudinally thereof. The control element includes a proximal end which extends beyond the band member for allowing remotely controlled release of the securing member from the recess by movement of the bolt. Advantageously, the device further includes a guiding plate, located within the band member of on one side of the recess, for guiding the movement of the bolt, and a holding plate located within the band member on the other side of the recess, for retaining the free end of the bolt.

The expandable section preferably comprises an expandable member corresponding to that discussed above, i.e., one extending around substantially the entire circumference of the band portion, i.e., the portion that, in use, encircles the stomach wall.

A remotely disposed fluid injection unit is preferably provided which is in fluid connection with the expandable section through the band member such that the size of the stomach opening can be altered by adding or withdrawing fluid to cause expansion and retraction of the expandable section.

Advantageously, a barrier means is provided for preventing tissue from growing around the securing member. The barrier means preferably comprises a soft sponge-like silicone barrier element.

Preferably, a thin loop is formed around the securing member for ensuring a secure fit between the securing member and the recess.

In accordance with a further aspect of the invention, a method is provided for removing a band having an expandable section encircling a stomach which forms a circle of a predetermined fixed diameter by employing a securing means to retain a locking element projecting from said band at a location near the distal end of said band into a recess formed at an intermediate location along said band, the method comprising the steps of: retracting the securing means so as to release the locking element from the recess; cutting the band close to the recess on a side of the recess opposite the expandable section, the securing means being sufficiently retracted such that it is not severed by the cutting; removing the cut portion not containing the recess and the expandable section through a small incision; and laparoscopically removing the remainder of the band containing the recess and the expandable section.

In accordance with an additional aspect of the invention, a method is provided for removing a band encircling a stomach which forms a circle of a predetermined fixed diameter by employing a securing means to retain a locking element projecting from said band at a location near the distal end of said band into a recess formed at an intermediate location along said band, the method comprising the steps of: completely removing the securing means through a small incision, thus also releasing the locking element from the recess; and laparoscopically removing the band.

Preferably, for either method described above, the further step of removing an injection port in communication with the expandable section through the small incision prior to the laparoscopically removing step is also performed.

In accordance with yet another aspect of the invention a method is provided for laparoscopically implanting a gastric band device including an encircling band portion which, in use, encircles a stomach so as to form a restricted stoma opening for limiting food intake to the lower digestive portion of the stomach, the gastric band device including an expandable section secured to the encircling band portion for varying the size of the stomach opening, an elongate band portion incorporating a remotely operable securing means for, when the device is implanted, retaining a locking element projecting from the gastric band device at a location near the distal end of the encircling band portion in a locking position wherein the locking element is received in a recess formed at an intermediate location along the gastric banding device so that, when the band is implanted, the encircling band portion forms a circle of a predetermined fixed diameter around the stoma opening, and expansion control means, communicating with the expandable section through a channel formed in the elongate band portion, for controlling expansion and contraction of said expandable section, said method comprising the steps of:

using an endoscope introduced into an cannula to dissect tissue surrounding the stomach to provide a path for the elongate band portion of the gastric band device;

laparoscopically introducing the gastric band into the abdominal cavity such that said encircling band portion encircles the stomach and said locking element is inserted in said recess so that said encircling band portion forms a circle of predetermined fixed diameter around said stoma opening of the stomach;

operating said securing means to lock said locking element in said recess; and implanting said expansion control means in the abdominal muscle wall.

Other features and advantages of the invention will be set forth in, or apparent from, the following detailed description of preferred embodiments of the invention.

BRIEF DESCRIPTION OF THE DRAWINGS

The invention will now be described in further detail with reference to the accompanying drawings, wherein.

DESCRIPTION OF THE PREFERRED EMBODIMENTS

Figure 1:
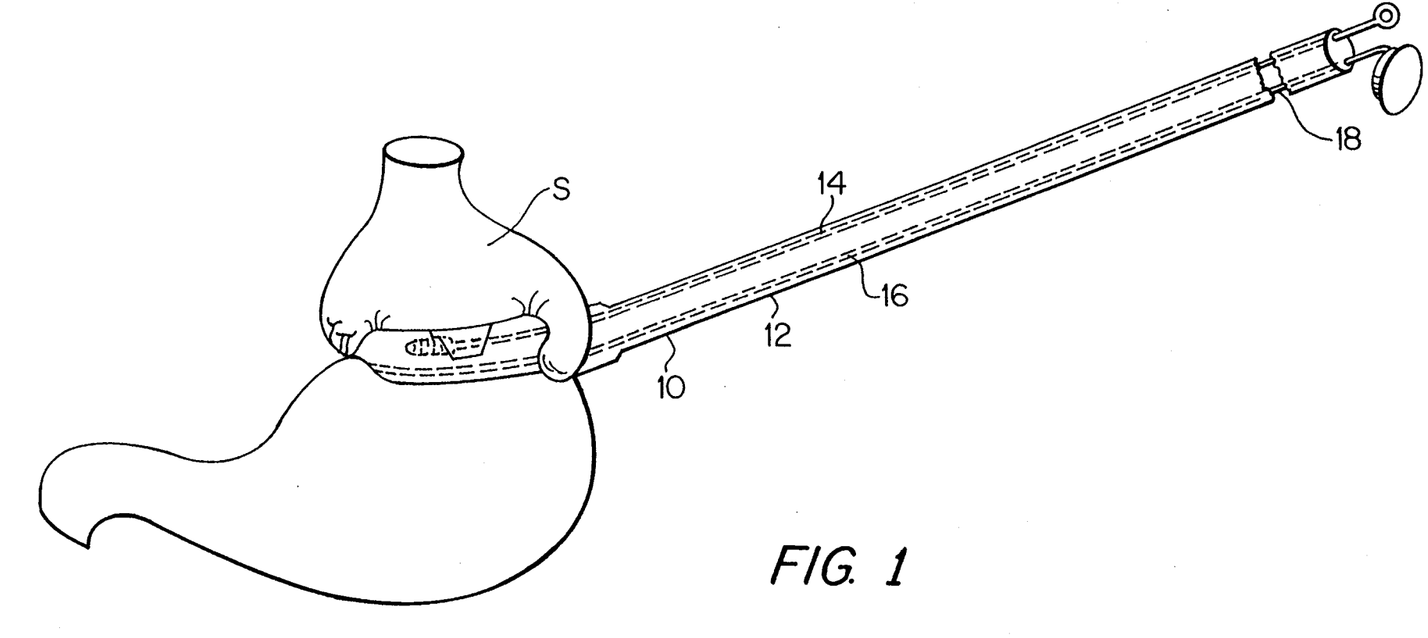
FIG. 1 is a perspective view of the modified laparoscopic SASGB device of the present invention as placed in position around a stomach.

Referring to FIG. 1, a SASGB device, generally denoted 10, is shown in place around a stomach S. More particularly, the device 10 comprises a band 12 which includes a loop or encircling portion (which is not fully visible in FIG. 1) that, in use, fully encircles the stomach S so as to form stoma opening at the loop portion, thereby restricting food intake to the lower digestive portion of the stomach S. As described in more detail below, a channel 14 allows fluid to be transmitted to or removed from an expandable section or portion of the device 10 which is not visible in FIG. 1, while a further channel 16 contains an elongate control member 18 for a securing or locking mechanism for encircling loop.

The SASGB device 10 of FIG. 1 is shown in more detail in FIGS. 2 to 5. As shown in these figures, the band locking device referred to above includes an outwardly projecting securing or locking member 20 located towards the tip or free (distal) end of the band 12 and a recess or slot 22 in which locking member 20 is received, as described hereinafter. The abovementioned expandable or inflatable section of the band 12 is denoted 24, and extends along the entire band portion 12a which, in use, encircles the stomach, as is perhaps best seen in FIG. 4. The channel 14 itself forms a passage, or accommodates a separate tube 26, which connects the expandable or inflatable section 24 of the band 12 with an injection unit 28 for injecting or removing solution in order to adjust the size of the stoma opening. This solution is a physiologically compatible fluid, such as saline.

Figures 3A, 3B, 4:
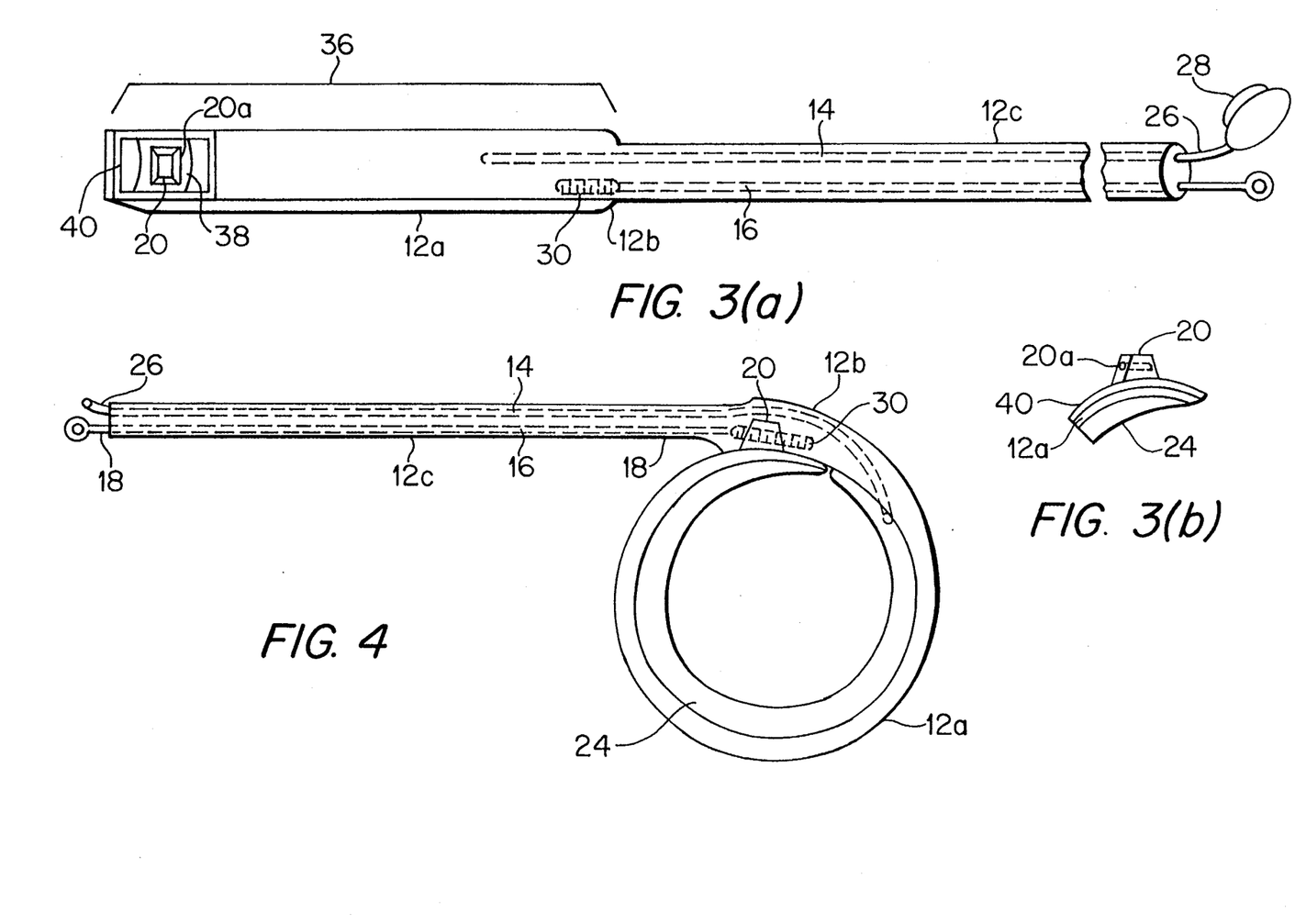
FIG. 3(a) is a top plan view of the device of FIG. 2(a)
FIG. 3(b) is a side view of the locking element of the device of FIG. 2(a)
FIG. 4 is a side view of the device of FIG. 2(a) with the band locked in place to form a circle or loop.

Considering the securing or locking mechanism in more detail, the recess or slot 22 located in an intermediate band portion 12b is shaped to accommodate locking member or element 20 therein when the distal end of band 12 is formed into a loop as shown in FIG. 4. The locking element 20 has a hole 20a therein through which a screw threaded locking bolt 30 formed at the end of the control member 18 introduced through channel 16 (and best seen in FIG. 4) is inserted, thus securing the locking member 20 in the recess or slot 22. As can best be seen in FIG. 2(b), a first, holding or retaining plate 32 having an opening 32a therein is provided near the free or distal end of channel 16 adjacent to recess 22 to hold the tip of the threaded screw bolt 30. Plate 32 is bonded into the band 12. The opening 32a in the plate 32 is sized to fit or match the shape of the tip of the screw bolt 30 and is not threaded. A second, guiding plate 34 has an opening 34a therein the diameter of which equals the diameter of the bolt 30 without the screw thread. Plate 34 is bonded into band 12 on the other side of the slot 22. The control member 18, which terminates at the distal end thereof in the threaded locking bolt 30, extends at the opposite proximal end thereof beyond the length of the band 12, thus enabling movement of bolt 30, and hence locking of the distal end of the band 12 in recess 22, to be controlled remotely.

Figure 2A:
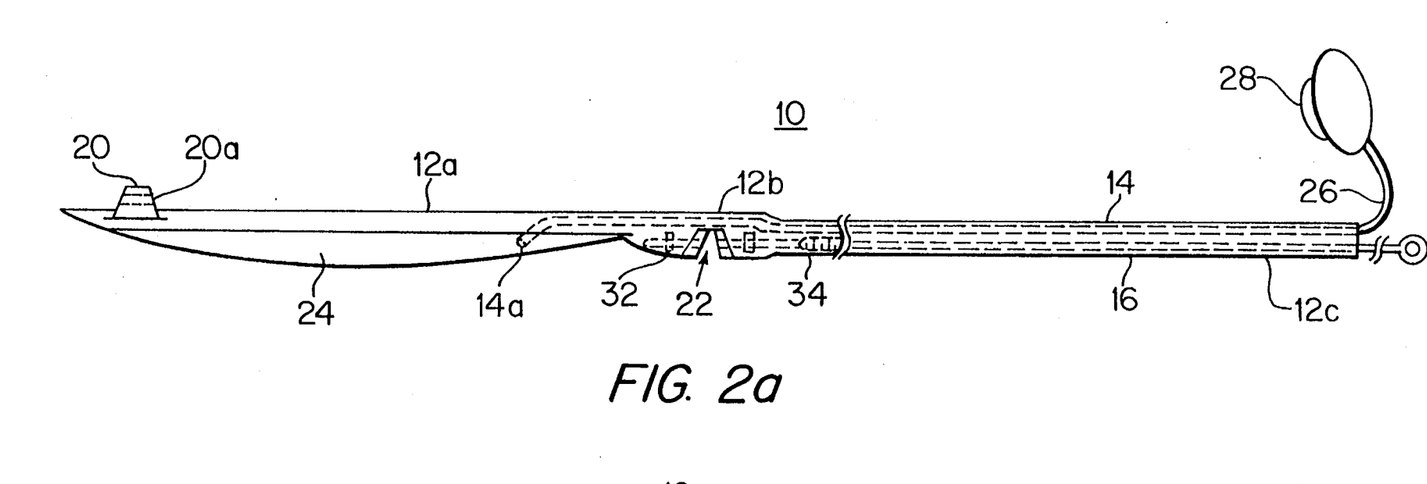
FIG. 2(a) is a side view of the SASGB device constructed in accordance with a preferred embodiment of the present invention, showing the device in an extended, rest state.
Figure 2B:
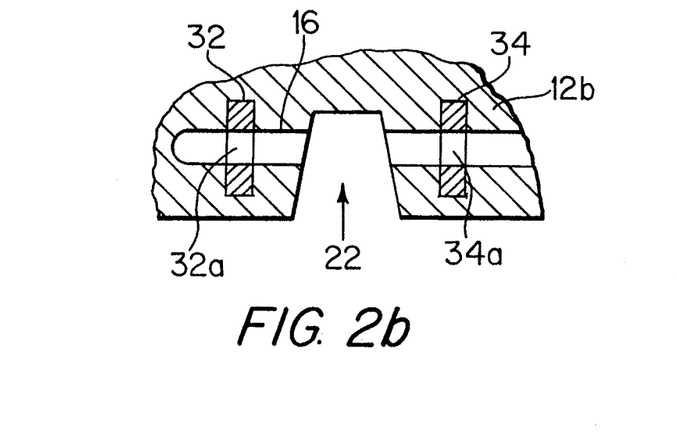
FIG. 2(b) is a cross sectional view of a detail of FIG. 2(a) showing the locking recess or slot.

As is shown in FIGS. 2(a) and 3(a), the band thickness of the receiving segment or portion of the band 12b is greater than the thickness of the remainder of the band. This increased thickness is necessary in order to accommodate the thickness of the locking element or projection 20 formed near the distal end of the band, while still allowing channel 14 to reach the inflatable portion 24.

In a specific, non-limiting but advantageous embodiment, the band locking element 20 and the band 12 itself are preferably made of silicone and, as described above, the former has an opening 20a with a screw type thread for locking the band 12 in place around the stomach. The proximal edge of the band locking element 20 is preferably 1½ centimeters from the tip or free end of the band. Further, the band locking element 20 is preferably of the truncated polygonal shape shown in the drawings and has a height of 4 millimeters and a length at its base of 6 millimeters. The inflatable section or part 24 is preferably reinforced and in the exemplary embodiment under consideration, the section 24 is 8 centimeters in length. Reinforcement of the sides of the inflatable part 24 is important in order to eliminate side bulging and to increase the circular inflation which is important in providing stoma calibration. The silicone covering the band 12 may be used for reinforcement. The tube 26 located within channel 14 is also preferably made of silicone. The retaining plate 32 and the guiding plate 34 are preferably made of silicone and are located 1½ centimeters from the recess or slot 22 on opposite sides thereof. Bolt 30 is advantageously made of silicone or plastic as is control element 18.

The band 12 is, as stated, preferably made of silicone and is wider than previously used bands, advantageously 13 mm. The band thickness of the portion of the band 12a covered by the inflatable section 24, i.e., that which encircles the stomach, is similar in thickness to previous bands, preferably 2 mm. The band thickness of the receiving segment is preferably between 4 to 6 mm. The band thickness of the elongate band portion 12c is preferably between 2 to 4 mm, and is roughly one-half to two-thirds of the thickness of the receiving segment. The front part of the band 12, i.e., band portions 12a and 12b, indicated by bracket 36, is preferably reinforced with a mesh of Dacron polyethylene terephthalate. The remaining elongate band portion 12c is preferably not reinforced so that it is soft and flexible.

Figures 5A, 5B:
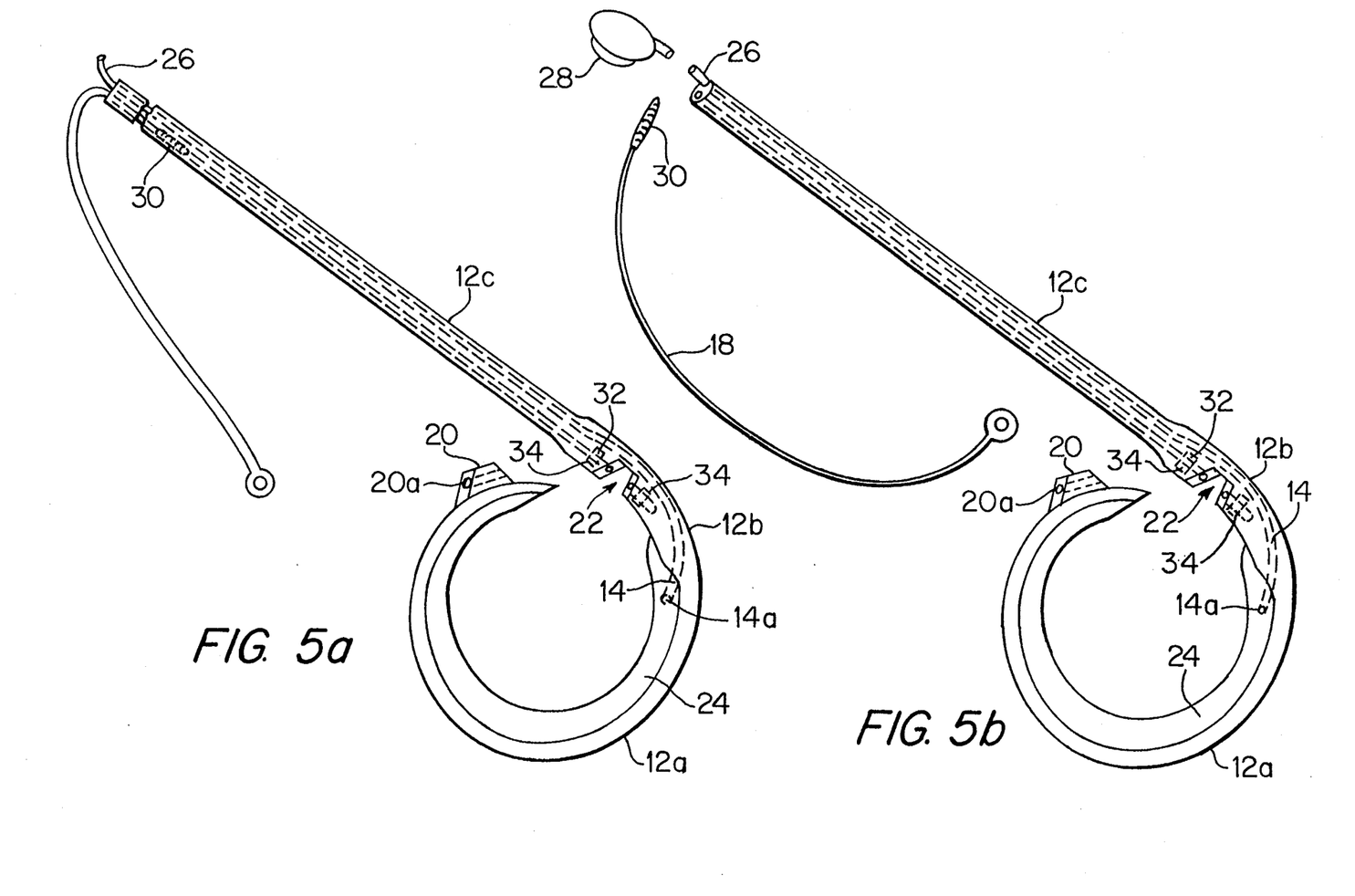
FIG. 5(a) is a side view of the device shown in FIG. 2(a) with the band unlocked.
FIG. 5(b) is a side view of the device shown in FIG. 2(a) with the band unlocked and the locking bolt and associated control member completely removed.

In order to better accommodate the positioning of the band parts in the locking position, a thin loop of silicone, indicated at 38 in FIG. 3(a), is bonded around the projecting barrier or locking element 20. Additionally, a soft sponge-like silicone guard portion, indicated at 40 in FIG. 3(a) and FIG. 3(b), is advantageously placed around the projecting locking element 20 in order to prevent the capsule tissue, i.e., tissue forming a capsule around the band, from growing into that space. Such capsule tissue may cause some limited resistance when the band is removed without major surgery. Linear markings (not shown) may be placed on both parts of the band 12 that are joined together as shown in FIGS. 4, 5(a) and 5(b) so that when the markings are matched with each other, an indication is provided that the locking parts are in correct position. As noted above, FIG. 4 shows the device in the fully locked position with the bolt 30 fully extended through the projection locking element 20 and into the holding or retaining plate 32. The diameter of the "locked" band, i.e., the band in the closed position shown in FIG. 4, is preferably 4 cm, although a diameter between about 4 to 6 cm could be acceptable.

As set forth above, the band device 10 is particularly adapted to be laparoscopically implanted. In this regard, although the device disclosed in application Ser. No. 08/019,302 filed on Feb. 18, 1993, can also be laparoscopically implanted and, in this regard, is not limited to any particular method of implantation, the differences between the device of the present application and that of the earlier application, and more specifically, the increased flexibility and the thinner, more streamlined shape of the gastric band device of the invention facilitate laparoscopic implantation thereof. In general, the laparoscopic procedure used to implant the device is that disclosed in Ser. No. 07/179,123, filed on Jun. 20, 1991, the content of which is hereby incorporated by reference. In fact, the only differences in the procedure flow from the differences in the two band devices. In this regard, the band 12 of the invention would be placed around the stomach in the same general way after using an endoscope introduced into a cannula to dissect tissue surrounding the stomach so as to provide a path for the gastric band 12. However, in contrast to the earlier device, the remotely controlled movement of the control member 10 would be used to provide locking of the locking mechanism (comprising locking element or projection 20 and slot or recess 22), thus fixing band 12 in place in an encircling relation around the stomach. The injection unit 28, located at the end of the band 12, would be implanted in the abdominal wall muscles, as in the prior application, and the overall laparoscopic procedure would likewise be similar.

Considering methods of removal of the band 12 after implantation, as indicated above, the living body in which the device of the invention is inserted creates a thin capsule around the implanted silicone band 12 that is not adhered to the band 12. By exposing the site of the injection unit implantation, i.e., the site at which unit 28 is disposed within the abdominal wall muscles, the proximal end of the band 12 is exposed as well. Through displacement of the threaded bolt 30 by remotely controlled movement of control member 18, the band locking mechanism (comprising locking element 20 and slot or recess 22) can be released.

In accordance with one method of removing the band, the control member 18 and the locking bolt 30, which are stiff and difficult to cut relative to elongate band portion 12c, are removed sufficiently from the band 12, as shown in FIG. 5(a), so that the elongate portion 12c, i.e., the portion not containing the recess 22 or the expandable section 24, may be easily cut close to recess 22, without cutting the control member 18. This allows the relatively thin band portion 12c to be removed with the injection unit 28 through the site of the injection unit implantation, preferably in the abdominal muscles near the skin. The remainder of the SASGB, i.e., portion 12b containing the recess 22 and portion 12a containing the expandable section 24, can then be removed laparoscopically at the site of the these portions of the band 12, i.e. at the stoma opening.

Alternatively, referring to FIG. 5(b), the SASGB of the present invention can also be removed by completely removing the control member 18 from within the band 12 and by removing the injection port 28 through a small superficial incision. With these components removed, the entire SASGB, including the relatively thin elongate portion 12c, is then removed laparoscopically at the site of the stoma. One advantage of removing the band or a part thereof at the stoma is that the surgeon may wish to gain access to this area in any event in order to remove suturing at the stoma.

As should be evident from the foregoing, the band device 10 of the present invention is more effective than the prior art in uniformly controlling the size of stoma opening and, among other advantages, is less invasive to the stomach wall because of the use of the inflatable part 24 which covers the entire portion of band 12a that encircles the stomach. The use of the thinner elongate portion 12 also helps to relieve the discomfort felt by some patients when the elongate portion 12C is of a greater thickness.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A gastric banding device for forming a stoma opening in a stomach so as to restrict food intake to the lower digestive portion of the stomach, said device comprising:

an elongate band member including a band portion for, in use, encircling a stomach to form a stoma opening in the stomach, said band member including a free end and an intermediate portion having a thickness greater than the thickness of the remainder of said band member;

an expandable section secured to said band portion of said band member for varying the size of the stoma opening;

a securing member located near said free end of said band member and protruding outwardly therefrom;

a recess, formed in said intermediate portion of said band member, for receiving said securing member therein; and means, including a movable control member separate from said securing member, for positively retaining said securing member in said recess so that said band portion forms a circle of a predetermined fixed diameter around said stoma opening.

2. A gastric banding device as claimed in claim 1, wherein said central member comprises a moveable bolt for releasably retaining said securing member in said recess.

3. A gastric banding device as claimed in claim 2, wherein said securing member includes a threaded hole therein in which said bolt is received.

4. A gastric banding device as claimed in claim 2, wherein said bolt comprises a distal part of an elongate control element located within said band member and extending longitudinally thereof.

5. A gastric banding device as claimed in claim 2, wherein said control element includes a proximal end which extends beyond said band member for allowing remotely controlled release of securing member from said recess by movement of said bolt.

6. A gastric banding device as claimed in claim 2, further comprising a guiding plate, located within said band member of on one side of said recess, for guiding the movement of said bolt, and a holding plate located within said band member on the other side of said recess, for retaining the free end of said bolt.

7. A gastric banding device as recited in claim 1, wherein said expandable section comprises an expandable member extending around substantially the entire circumference of said band portion that, in use, encircles the stomach wall.

8. A gastric banding device as claimed in claim 1, wherein said expandable section includes reinforcement in the sidewalls thereof.

9. A gastric banding device as recited in claim 1, further comprising a remotely disposed fluid injection unit in fluid connection with said expandable section through said band member such that the size of the stoma opening can be altered by adding or withdrawing fluid to cause expansion and retraction of said expandable section.

10. A gastric banding device as claimed in claim 1, further comprising barrier means for preventing tissue from growing around said securing member.

11. A gastric banding device as claimed in claim 10, wherein said barrier means comprises a soft sponge-like silicone barrier element.

12. A gastric banding device as claimed in claim 1, further comprising a thin loop extending around a peripheral surface of said securing member which is received in said recess for ensuring a secure fit between said securing member and said recess.

13. A method for removing a gastric band device including an encircling band portion encircling a stomach so as to form a restricted stoma opening for limiting food intake to the lower digestive portion of the stomach, said gastric band device including an expandable section secured to said encircling band portion for varying the size of the stomach opening, an elongate band portion incorporating a remotely operable securing means for retaining a locking element projecting from said gastric band device at a location near the distal end of said encircling band portion in a locking position wherein said locking element is received in a recess formed at an intermediate location along said gastric banding device so that said encircling band portion forms a circle of a predetermined fixed diameter around said stoma opening, and expansion control means, located in the abdominal muscle wall at the proximal end of said gastric band device, for controlling expansion and contraction of said expandable section, said method comprising the steps of:

provinding an incision in the abdominal muscle wall at the location of said expansion control means;

retracting said securing means so as to release said locking element from said recess;

cutting said elongate band portion close to said recess on a side of said recess opposite said expandable section, with said securing means sufficiently retracted such that the securing means is not severed by said cutting, so as to produce a cut portion of said elongate band portion;

removing both said expansion control means and said cut portion of said elongate band portion through said incision; and laparoscopically removing the remainder of said gastric band device containing said recess and said expandable section at the location of said stoma opening.

14. A method for removing a gastric band device including an encircling band portion encircling a stomach so as to form a restricted stoma opening for limiting food intake to the lower digestive portion of the stomach, said gastric band device including an expandable section secured to said encircling band portion for varying the size of the stomach opening, an elongate band portion incorporating a remotely operable securing means for retaining an outwardly projecting locking element formed integral with and projecting from said gastric band device at a location at least near the distal end of said encircling band portion in a locking position wherein said locking element is received in a recess formed at an intermediate fixed distance along said gastric banding device from said locking element so that said encircling band portion forms a circle of a predetermined fixed diameter around said stoma opening, and expansion control means, located in the abdominal muscle wall at the proximal end of said gastric band device, for controlling expansion and contraction of said expandable section, said method comprising the steps of:

providing an incision in the abdominal muscle wall at the location of said expansion control means;

removing said expansion control means through said incision;

releasing said outwardly projecting locking element from said recess and completely removing said securing means from said gastric band device through said incision; and laparoscopically removing said gastric band device at the location of said stoma opening.

15. A method for laparoscopically implanting a gastric band device including an encircling band portion which, in use, encircles a stomach so as to form a restricted stoma opening for limiting food intake to the lower digestive portion of the stomach, said gastric band device including an expandable section secured to said encircling band portion for varying the size of the stomach opening, an elongate band portion incorporating a remotely operable securing means for, when the device is implanted, retaining an outwardly projecting locking element formed integral with and projecting from said gastric band device at a location at least near the distal end of said encircling band portion in a locking position wherein said locking element is received in a recess formed at an intermediate fixed distance along said gastric banding device from said locking element so that, when the band is implanted, said encircling band portion forms a circle of a predetermined fixed diameter around said stoma opening, and expansion control means, communicating with said expandable section through a channel formed in said elongate band portion, for controlling expansion and contraction of said expandable section, said method comprising the steps of:

using an endoscope introduced into an cannula to dissect tissue surrounding the stomach to provide a path for the elongate band portion of the gastric band device;

laparoscopically introducing the gastric band into the abdominal cavity such that said encircling band portion encircles the stomach and said locking element is inserted in said recess so that said encircling band portion forms a circle of a fixed diameter around said stoma opening of the stomach which is predetermined prior to insertion of the locking element into the recess by said fixed distance between the locking element and the recess;

operating said securing means to lock said locking element in said recess; and implanting said expansion control means in the abdominal muscle wall.

16. A gastric banding device for forming a stoma opening in a stomach so as to restrict food intake to the lower digestive portion of the stomach, said device comprising:

a band member including encircling band means for, in use, encircling a stomach in a single loop so as to form a stoma opening in the stomach;

an expandable section extending completely around the entire length of said encircling band means so that, in use, the expandable section fully encircles the stoma opening; and means for controlling expansion and contraction of said expandable section so as to control the size of the stoma opening;

said band means having a free end and said device further comprising a first interlocking securing means disposed at a first predetermined fixed position at least close to said free end and a second interlocking securing means, disposed at a second predetermined fixed position located at an intermediate portion along said band, for interlocking with said first interlocking securing means to provide securing of said free end of said band means to said intermediate portion of said band means at said second position so that the band means forms a single loop circle of predetermined fixed diameter around the stoma opening.

17. A gastric banding device as claimed in claim 16, wherein said expandable section comprises an elongate inflatable element having reinforced walls.

18. A gastric banding device as recited in claim 16, further comprising releasing means for remotely releasing said securing means.

19. A gastric banding device for forming a stoma opening in a stomach so as to restrict food intake to the lower digestive portion of the stomach, said device comprising:

an elongate band member including a band portion for, in use, encircling a stomach to form a stoma opening in the stomach, said band member including a free end, and securing means for securing the free end of said band member to an intermediate portion of said band member so that said band portion forms a circle of a predetermined fixed diameter around said stoma opening, said securing means comprising first and second fixed interlocking means formed integrally with the band member for, when interlocked, forming said band portion into said circle of predetermined diameter; and an expandable section secured to said band portion of said band member for varying the size of the stoma opening; said first interlocking means comprising a securing member located near the free end of said band member and protruding outwardly therefrom and said second interlocking means comprising a recess formed in said band member at said intermediate portion thereof for receiving said securing member therein.

20. A gastric banding device as claimed in claim 19, wherein said securing means further comprises retaining means separate from said securing member for positively retaining said securing member in said recess.

21. A gastric banding device as claimed in claim 20, wherein said retaining means comprises a moveable bolt.

22. A gastric banding device as claimed in claim 20, wherein said retaining means comprises a distal part of an elongate control element located within said band member and extending longitudinally thereof.

23. A gastric banding devices as claimed in claim 22, wherein said control element includes a proximal end which extends beyond said band member for allowing remotely controlled release of securing member from said recess by movement of said retaining means.

24. A gastric banding device as claimed in claim 21, wherein said bolt has a free end, said device further comprising a guiding plate, located within said band member of on one side of said recess, for guiding the movement of said bolt, and a holding plate located within said band member on the other side of the recess, for retaining the free end of said bolt.

25. A gastric banding device as recited in claim 19, wherein expandable section comprises an expandable member extending around the entire circumference of said band portion that, in use, encircles the stomach wall in a single loop.

26. A gastric banding device as claimed in claim 19, wherein said band portion of said band member is of a first thickness and the remainder of the band member is of a second, greater thickness.

27. A gastric banding device as claimed in claim 19, wherein said expandable section includes reinforcement in the sidewalls thereof.

28. A gastric banding device as recited in claim 19, further comprising a remotely disposed fluid injection unit in fluid connection with said expandable section through said band member such that the size of the stoma opening can be altered by adding or withdrawing fluid to cause expansion and retraction of said expandable section.

29. A gastric banding device as claimed in claim 19, further comprising barrier means on said band member for preventing tissue from growing around said securing member.

30. A gastric banding device as claimed in claim 29 wherein said barrier means comprises a soft sponge-like silicone barrier element.

31. A gastric banding device as claimed in claim 19, further comprising a thin loop formed around the securing member for ensuring a secure fit between said securing member and said recess.

32. A device as claimed in claim 19, wherein said securing means further comprises retaining means separate from said securing member for positively retaining said securing member in said recess.

33. A method for controlling the size of a stoma opening in a stomach so as to provide the restriction of food intake to the digestive portion of the stomach, said method comprising the steps of:
placing an elongate band around an exterior surface of a stomach so that a portion of the band encircles the stomach;
inserting a locking element formed integrally with and projecting outwardly from said band at a location near the distal end of the band into a recess formed at an intermediate location along the said band so as to form said band into a complete circle of fixed diameter around the stomach; and
positively securing said locking element in said recess using a retaining member separate from said locking element.

34. The method as recited in claim 33, further comprising varying the amount of fluid contained in an expandable section located on a surface of said band in contact with the exterior surface of the stomach so as to vary the size of the stoma opening.

35. The method as claimed in claim 33 wherein securing of said locking element in said recess comprises using a remotely located control member connected to said retaining member by a connector element extending along the length of said band to move said retaining member so as to lock said locking element in said recess.

36. The method as claimed in claim 33 further comprising using a remotely located control member connected to said retaining member by a connector element extending along the length of said band to move said retaining member so as to release said locking member from said recess.

37. A gastric banding device for forming a stoma opening in a stomach so as to restrict food intake to the lower digestive portion of the stomach, said device comprising:
an elongate band member including a band portion for, in use, encircling a stomach to form a stoma opening in the stomach, said band member including a free end, and securing means for securing the free end of said band member to an intermediate portion of said band member so that said band portion forms a circle of a predetermined fixed diameter around said stoma opening, said securing means comprising first and second fixed interlocking means formed integrally with the band member for, when interlocked, forming said band portion into said circle of predetermined diameter; and a retaining member separate from said first and second interlocking means for positively securing said first and second interlocking means together so as to prevent unlocking thereof; and an expandable section secured to said band portion of said band member for varying the size of the stoma opening.

38. A device as claimed in claim 37 further comprising a control member located at the proximal end of said band member and connected to said retaining member by a connector element extending along the length of said band member for controlling movement of said retaining member.

39. A device as claimed in claim 37 wherein one of said first and second interlocking means comprises a projection and the other of said first and second interlocking means comprises a recess and wherein said retaining member engages said projection in said recess to provide locking of said projection in said recess.

40. The device as claimed in claim 39 wherein said retaining member comprises a movable bolt.

* * * * *